(12) United States Patent
Friedli

(10) Patent No.: US 8,974,435 B2
(45) Date of Patent: Mar. 10, 2015

(54) ADMINISTRATION DEVICE HAVING A BUTTON WITH TOUCH SENSOR

(75) Inventor: Kurt Friedli, Lyssach (CH)

(73) Assignee: Roche Diagnostics International AG, Rotkreuz (CH)

(*) Notice: Subject to any disclaimer, the term of this patent is extended or adjusted under 35 U.S.C. 154(b) by 499 days.

(21) Appl. No.: 12/912,817

(22) Filed: Oct. 27, 2010

(65) Prior Publication Data
US 2011/0270219 A1    Nov. 3, 2011

Related U.S. Application Data

(63) Continuation of application No. PCT/EP2009/003089, filed on Apr. 29, 2009.

(30) Foreign Application Priority Data

Apr. 30, 2008  (EP) .................................. 08155464

(51) Int. Cl.
*A61M 31/00*  (2006.01)
*A61M 5/20*  (2006.01)
(Continued)

(52) U.S. Cl.
CPC .............. *A61M 5/20* (2013.01); *A61M 5/14244* (2013.01); *A61M 2005/2013* (2013.01); *A61M 2005/2073* (2013.01); *A61M 2205/13* (2013.01); *A61M 2205/276* (2013.01); *A61M 2205/3317* (2013.01); *A61M 2205/502* (2013.01); *A61M 2205/581* (2013.01); *A61M 2205/582* (2013.01);
(Continued)

(58) Field of Classification Search
CPC ............. A61M 2005/2013; A61M 2005/2073; A61M 2205/13; A61M 2205/276; A61M 2205/3317; A61M 2205/502; A61M 2205/581; A61M 2205/582; A61M 2205/583; A61M 2205/60; A61M 2205/8212; A61M 5/14244; A61M 5/20; H01H 2003/0293
USPC .......................................... 604/65, 506, 187
See application file for complete search history.

(56) References Cited

U.S. PATENT DOCUMENTS

2002/0133113 A1* 9/2002 Madsen et al. .................. 604/65
2007/0186923 A1  8/2007 Poutiatine et al.

FOREIGN PATENT DOCUMENTS

EP  1847287 A1  10/2007
WO  9907425 A1  2/1999
(Continued)

OTHER PUBLICATIONS

International Search Report, Application No. PCT/EP2009/003089 filed Apr. 4, 2009, completion of ISR is Aug. 6, 2009, pp. 1-10.
(Continued)

*Primary Examiner* — Edelmira Bosques
*Assistant Examiner* — Hamza Darb
(74) *Attorney, Agent, or Firm* — Dinsmore & Shohl LLP

(57) ABSTRACT

Administration devices for supplying an injectable or infusible product into an organism include a reservoir for storing the product, a supply device for supplying the product from the reservoir into the organism, a controller to control operation of the administration device, a button communicatively coupled to the controller to initiate at least one action of the administration device and a touch sensor that generates an activation signal, wherein the touch sensor is incorporated into the button or is disposed in the vicinity of the button and is communicatively coupled to the button and/or the controller.

20 Claims, 4 Drawing Sheets

(51) Int. Cl.
*A61M 5/142* (2006.01)
*H01H 3/02* (2006.01)
*H03K 17/955* (2006.01)
*H03K 17/96* (2006.01)

(52) U.S. Cl.
CPC ...... *A61M 2205/583* (2013.01); *A61M 2205/60* (2013.01); *A61M 2205/8212* (2013.01); *H01H 2003/0293* (2013.01); *H03K 17/955* (2013.01); *H03K 17/962* (2013.01); *H03K 2217/94052* (2013.01)
USPC .............................. 604/506; 604/187; 604/65

(56) References Cited

FOREIGN PATENT DOCUMENTS

| WO | 2005077441 | A2 | 8/2005 |
| WO | 2006114288 | A1 | 11/2006 |
| WO | 2007088444 | A1 | 8/2007 |

OTHER PUBLICATIONS

Written Opinion, Application No. PCT/EP2009/003089 filed Apr. 4, 2009, completion of ISR is Aug. 6, 2009, pp. 1-8.

* cited by examiner

ADMINISTRATION DEVICE HAVING A BUTTON WITH TOUCH SENSOR

CROSS REFERENCE TO RELATED APPLICATIONS

This application is a continuation of International Application No. PCT/EP2009/003089 filed Apr. 29, 2009 which claims priority to European Patent Application No. 08155464.4 filed on Apr. 30, 2008 which are incorporated by reference herein.

TECHNICAL FIELD

This specification relates to an administration device for supplying an injectable or infusible product into an organism, such as a patient, and in particular to administration devices or self-administration devices having a button with touch sensor.

BACKGROUND

Administration devices or self-administration devices can be used to serve diabetes patients. An administration device for the self-administration of medicines such as insulin may be placed in a patient's pocket and connected to the patient's organism to supply a suitable dose of medicine, in particular insulin, to the patient. The user interface provided for the patient can consist of a display, keys and/or buttons for entering instructions for a control circuit included in the device. Via the user interface, the administration device may be programmed to allow for information such as the administration history or the remaining medicine amount in a medicine reservoir to be recalled and allow for the administration of medicine boli to be initiated.

However, since the administration device can work automatically through the control of a control device such as a micro controller, it may not be necessary for the display to be constantly active. Furthermore, the display may require a lot of electrical energy, hence if the display is in operation for a long time, it may be necessary to include large batteries or accumulators in the device. Accordingly, an attempt should be made to activate a display only when it is needed.

In some devices, the function of activating the display can be performed via a dedicated button. However, providing the additional button may be an obstacle to minimize the size of the overall device. Alternatively, the display may be activated whenever any button or key is pressed, thus potentially increasing the power consumption of the display.

Administration devices, such as those used in diabetes therapy, can be carried concealed from view such as by storing them in a trousers pocket. Furthermore, these administration devices can be programmed and/or manipulated by pressing keys or buttons through the trousers fabric based on audible and/or tactile feedback signals provided by the administration device. This may allow the patient to operate the device and in particular to initiate the administration of medicine boli with the device being concealed from view. If the device is operated in this way, activating the display may be unnecessary.

However, since concealable administration devices can be carried in a clothes pocket, such as a trousers pocket, as described above, it is possible that the keys or buttons become activated through arbitrarily and unintended bumping which may result in, among others things, an unintended administration of medicine doses. In this context, it has to be taken into account that an administration device has to administer a number of pre-adjustable doses, so-called basal doses, which have to be administered in accordance with the therapeutic needs of the patient according to a predefined schedule in a substantially continuous way. In addition, the patient may typically need additional doses, so called bolus doses, depending on particular circumstances and events which will vary from day to day, such that as the correction of high blood glucose values or food intake. Thus, the administration device may allow for the administration of such additional doses in an easy and discrete way, using the buttons or keys which are provided in order to operate the device. To prevent the unintended administration of medicine doses which may cause severe medical consequences due to buttons or keys being pressed unintentionally, for example by a key carried in the same pocket as the device, prior-art administration devices can be provided with at least two keys or buttons which have to be operated in sequence and within a particular time in order to administer a bolus dose. This, however, can increase the operational complexity and decrease the user comfort in particular if the administration device is operated concealed from view.

Conversely, administration can unintentionally occur if a button becomes instable due to a defect, e.g. has a loose connection or contact element since this again may cause a large number of unintended operations of a the unstable button, resulting in the administration of a large unintended dose with all its negative consequences. Occurrence of this situation may be prevented by providing at least too buttons which have to be operated in sequence as described above.

SUMMARY

In one embodiment, an administration device for supplying an injectable or infusible product into an organism is provided. The administration device can include a reservoir for storing the product, a supply device for supplying the product from the reservoir into the organism, a controller to control operation of the administration device, a button communicatively coupled to the controller to initiate at least one action of the administration device and a touch sensor. The touch sensor can generate an activation signal, wherein the touch sensor is incorporated into the button or is disposed in the vicinity of the button and is communicatively coupled to the button and/or the controller.

In another embodiment, a method for controlling operation of an administration device is provide. The method can include detecting if a touch sensor is activated, wherein the touch sensor is incorporated into a button or being disposed proximate the button, and wherein activating the touch sensor generates an activation signal, detecting if the button is being actuated, and initiating an action of the administration device in dependence of the touch sensor being activated or not activated and the button being pressed or not pressed.

In yet another embodiment, an administration device for supplying an injectable or infusible product into an organism is provided. The administration device can include a reservoir for storing the product, a supply device for supplying the product from the reservoir into the organism, a controller to control operation of the administration device, a button communicatively coupled to the controller to initiate at least one action of the administration device and a touch sensor. The touch sensor can generate an activation signal, wherein the touch sensor is incorporated into the button or is disposed in the vicinity of the button and is communicatively coupled to the button and/or the controller, wherein the touch sensor is a capacitive sensor or an inductive sensor, and wherein the button is enabled by the activation signal.

BRIEF DESCRIPTION OF DRAWINGS

The embodiments set forth in the drawings are illustrative and exemplary in nature and not intended to limit the subject matter defined by the claims. The following detailed description of the illustrative embodiments can be understood when read in conjunction with the following drawings where like structure is indicated with life reference numerals and in which:

FIG. 2b depicts a partial sectional view of the administration device of FIG. 2a;

Figure 1:
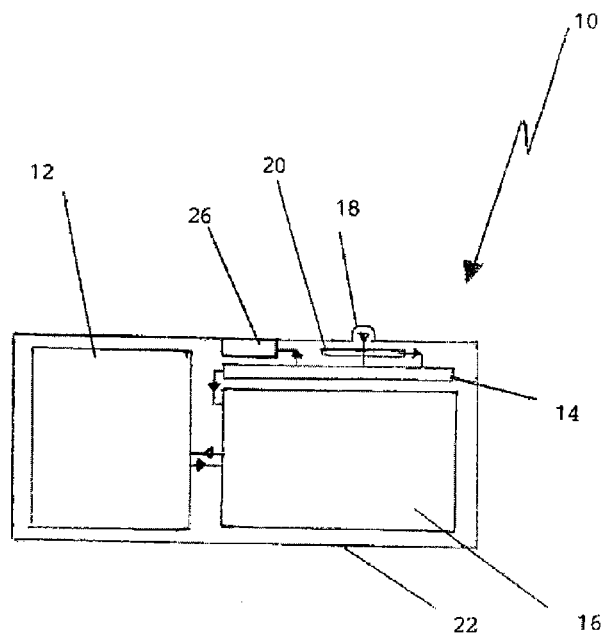
FIG. 1 schematically depicts an administration device according to one or more embodiments shown and described herein.

In the drawings, the same reference numbers have been assigned to identical parts or parts which have at least substantially the same function. Accordingly, the respective parts need not be explained anew in connection with each figure, since the explanation of a part in one figure can be applied to other figures.

DETAILED DESCRIPTION

Administration devices can generally comprise a reservoir, a supply device, a controller, a button and a touch sensor. The touch sensor can generate an activation signal, wherein the touch sensor is incorporated into a button or is located in the vicinity of a button, such as in an area neighbouring and/or partly or fully surrounding the button. For a touch sensor that is arranged in this way, the activation signal may be generated if a patient's finger physically touches the button or it is close enough to the button such that it can be assumed that the patient intends to operate the button. That is, the same movement of the patient's finger may first cause the touch sensor to generate the activation signal, followed by pressing the button. By discontinuing the motion, the patient may further cause the activation signal to be generated without subsequently pressing the button. The activation signal may not be generated if the administration device, in particular a preferably present housing of the administration device, is touched at a position remote from the button.

As used herein, the terms "key" and "button" are used in their meaning of an electro-mechanical switching element, wherein a operation element of the key or button must be actuated (e.g., pressed) with a certain fore and/or travel a distance for changing the state of the switching element. For this action, the terms "actuating," "operating" and "pressing" are used synonymously. The term "touch sensor" is used in the meaning of a sensor that may need to be touched to be activated or requires an activation object, such as a finger, in its near proximity, of e.g., about 1 mm or below. A touch sensor is referred to as being "activated" if it generates an activation signal, analogue to a button which is pressed. In contact to a button, operation of a touch-sensor does not involve a mechanical contact and accordingly requires no travel distance to be operated. Furthermore, in this specification, the "administration device" in accordance with the different embodiments of the present disclosure is also referred to as an "infusion device" for short.

Referring now to FIG. 1, an infusion device 10 (i.e., an administration device) includes an infusion section 12 which can comprise a reservoir for a medicine. In one embodiment, such as when the infusion device 10 is used for the therapeutic treatment of diabetes, the reservoir can store insulin. A supply means, such as a pump, may also be provided in order to supply predetermined doses of the medicine through a conduit into the patient's body (not shown). In one embodiment the supply means can comprise a piston which is accommodated in the reservoir, wherein the reservoir can be replenished. In addition, a motor may be coupled via a gear to the piston by a piston rod to move the piston in the direction of the centre axis of the reservoir, which may have a cylindrical shape, to push the medicine out of the reservoir. However, in other embodiments, other types of supply means and/or reservoirs may be used in the alternative or in addition. For example, in one embodiment, the supply means may comprise a micro membrane pump. In another embodiment, the supply means may comprise a peristaltic pump head. In yet another embodiment, the reservoir may be formed by a flexible bag, a pouch, or the like.

Figure 2A:
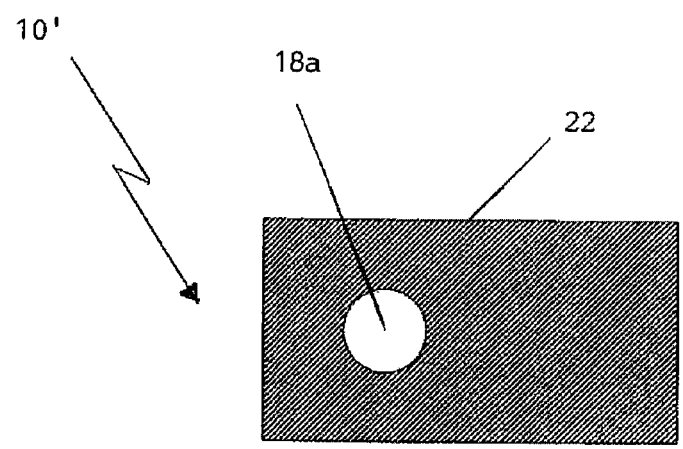
FIG. 2a depicts a plan view of another administration device according to one or more embodiments shown and described herein.
Figure 2B:
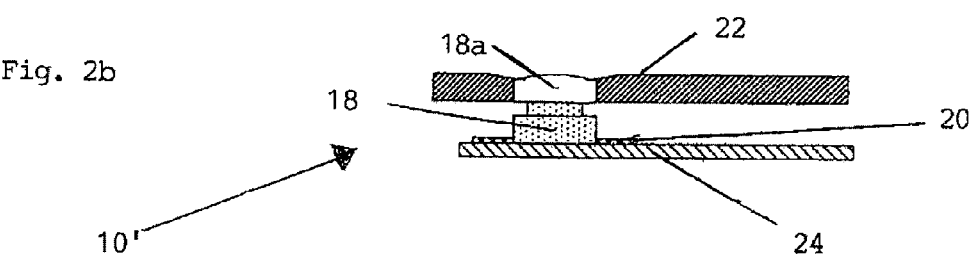

Referring now to FIGS. 1, 2a and 2b, a power source may also be included for supplying power to the motor and/or other parts of the infusion device 10. For example, the power source may be used to supply power to a controller 14, a display 16, a button 18, a touch sensor 20 incorporated into the button 18 and/or a printed circuit board 24. The controller 14 can also include a processor, a memory portion including a part where non-erasable control data are stored, such as a ROM memory, and a RAM and/or a reprogrammable memory such as an EEPROM, a flash memory or the like. The controller 14 can be accessed via the button 18, and data or information inputted via the button or requested from the controller can be indicated on the display 16.

A vibrator, a buzzer or loudspeaker or a combination thereof can be used to provide a recognisable signal to the operator or patient. In one embodiment, instead of a loudspeaker or buzzer 26, a visual signal may be used which can be emitted by an LED or other device that provides a signal recognised by a person such as a user or patient. The housing 22 of the infusion device 10 can accommodates all the different components of the infusion device 10. Furthermore, the housing 22 can be formed from different materials such as plastics and/or metal. In one particular embodiment, the housing may be formed from a material, and in particular a soft material, which does not shield or deflect electrical, magnetic or electromagnetic fields. In another embodiment, the housing may be disposed proximate the button 18.

In one embodiment, the touch sensor 20 can be directly coupled to the button 18. Such an embodiment allows for the enablement or disablement the push button 18 via the button. In this case, the touch sensor 20 can be considered as being in series with the button 18. In an alternative embodiment, the touch sensor 20 can be coupled to the controller 14. Such an embodiment allows for the enablement or disablement the button 18 via the controller 14. Additionally or alternatively, the enabling or disabling the button 18, the touch sensor 20 can also activate or deactivate the display 16.

When the touch sensor 20 is activated by an object, such as the earthed finger of an operator or patient, the controller 14 can control the loudspeaker, buzzer, LED 26 or the like to output a recognisable signal. This signal can be used to inform the operator or patient that the button 18 has been actuated in order to input data, request data, or the like, or and/or that the display 16 has been activated to display information.

Referring now to FIGS. 2a and 2b, a second embodiment of the administration device is illustrated. The top view in FIG. 2a illustrates the housing 22, which can be made from a hard plastic material, metal or other suitable material or materials which are resistant to mechanical shocks. A soft material portion 18a is further provided, which can allow for an operator to actuate (e.g., push) the button 18 shown in FIG. 2b, and which also enables an electrical field to extend through the soft material portion 18a, such that a person's finger can interact with the electrical field generated by the sensor 20 which, in the present case, can be a capacitive sensor. Accordingly, if an earthed portion of a person's body, for example a finger, approaches the sensor 20 of the infusion device 10', and the interaction is strong enough, the sensor 20 can output an activation signal that enables the button 18. In one embodiment, both the button 18 and the sensor 20 can be mounted on a printed circuit board which can also support the electrical circuits of the controller 14, and the touch sensor extends laterally out from the bottom of the button against the flat printed circuit board and is adhered to the flat printed circuit board.

The touch sensor 20 may further be used to input control data, such as an administration schedule, or request the display of data. In one embodiment, this can be achieved using a particular code which is inputted by the operator or the patient. For instance, the patient can approach and/or actuate the soft material portion two or three times, which is the code for activation, such that the code is accepted and the controller outputs a recognisable signal via the loudspeaker, buzzer or LED 26 (as illustrated in FIG. 1, in order to inform the patient that the input state has been activated.

In another embodiment, it may be possible to activate different input states or initiate different actions of the infusion pump 10 using different codes. For example, entering a code may be required for safety-critical operations such as reprogramming or modifying the basal administration schedule.

Figure 3:
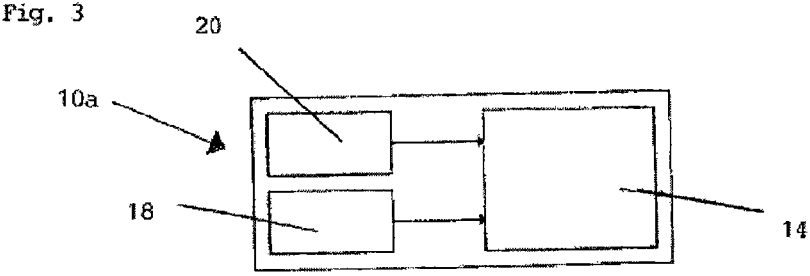
FIG. 3 schematically depicts parts of an administration device according to one or more embodiments shown and described herein.

Referring now to FIG. 3, a part of the infusion device 10a is illustrated. Specifically FIG. 3 illustrates the controller 14, the touch sensor 20 and the button or push button 18. In the illustrated in FIG. 3, if the sensor 20 outputs an activation signal, then the controller 14 can enable the button 18 or accepts signals inputted via the button 18 for causing the device to conduct an action (such as the administration of a medicine bolus). As discussed above, it is also possible for the controller 14 to enable the button 18 only for a predetermined but adjustable period of time (such as, for instance several seconds), in order to prevent an unintended activation of the sensor 20 that would possibly lead to signals being accepted from the button 18 over a long period of time, which could cause a bolus dose to be unintentionally administered.

Figure 4:
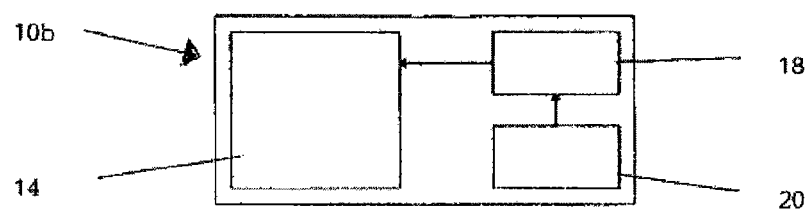
FIG. 4 schematically depicts parts of another administration device according to one or more embodiments shown and described herein.

Referring now to FIG. 4, in another embodiment of the device 10b, an activation signal generated by the sensor 20 can directly enable the button or push button 18. Such an embodiment may thus allow an operator or patient to input data or requests into the controller 14 via the button 18 and/or to cause the device to conduct an action, for example a medicine bolus administration. In such an embodiment, the touch sensor 20 and the button 18 can be considered as being electrically arranged in series.

The infusion devices can thereby incorporate the idea that a button of an administration device being pressed directly by an operator or patient, typically by a finger which comes into contact with the button, is representative for a different situation as compared to the button being pressed by a different object, such as a cloths fabric or a key which is stored in the same pocket as the infusion device, and should therefore result in different reactions of the administration device upon the button being pressed.

By utilizing such a touch sensor which generates an activation signal, it is possible to activate a display of the device. It is therefore possible to both initiate a device action, such as the administration of a medicine bolus, and to active the display, if the button is operated by a finger, and to further initiate the same or a different device action if the button is operated in a different way than by a finger. For such an embodiment, it may be derived that activating the display is desired if the patient directly accesses the device with a finger and activating the display is not desired if the button is operated by the patient in a different way (such as through clothes). Since significant device energy is not necessarily consumed by the display, but rather a display backlight, the display may alternatively be constantly activated, that is, show information, while the display backlight is activated as described above. For this type of embodiment, the term "activation" in the context of a display refers to the display backlight. This type of embodiment may allow for small energy consumption since the display is only activated when actually needed.

Furthermore, since there may be situations in which activation of the display is desirable even though the button has been pressed with an object different from the finger, for example with a glove, an additional button for manually activating the display may additionally be present.

In another embodiment, the button may initiate an action of the device, such as the administration of a medicine bolus, only if the button is pressed by a finger (i.e., only with the activation signal being generated), and does not initiate this action if the button is operated in a different way, (i.e., with the activation signal not being generated). This may be the case if the button is pressed by further object such as when a key is carried in the same pocket as the administration device or the button of the administration device is instable due to a defect. This may allow for maintaining the safety requirements of infusion devices while allowing actions such as initiating a medicine bolus administration with a single button. In such an embodiment, the button may be enabled (i.e. actuated) by the activation signal. A button is "enabled" if pressing or operating the button results in an action being conducted by the device. In contrast, a button is "disabled" if pressing or operating the button does not result in this action being conducted by the device. Such an embodiment can assist in safety with respect to unintended medicine bolus administration in combination with user convenience and discrete operation.

For clarity reasons, it is assumed here and in the following that the administration of a medicine bolus may be directly initiated by pressing a button of the device. This can be the case if medicine boli of fixed amount have to be administered. In some embodiments, however, the button may be pressed repeatedly and with each pressing of the button the medicine amount is increased by a given increment. Actual administration of the medicine may only be performed if the button has not been pressed for a predefined time. In addition, it may be possible to cancel the administration of a drug bolus before or during administration, e.g., by pressing a further button.

Besides the bolus administration, the button may be used for other instructions, such as general programming or requesting status information of the device, which are also to be conducted only when the button is enabled by the activation signal outputted by the touch sensor.

In accordance with one embodiment, it may be possible to incorporate the touch sensor into the button itself, such that it is not necessary to provide an additional area on the housing for the touch sensor. The housing of the administration device is preferably made of a soft material portion in order on the one hand to enable it to be water-proof, and also for generating an electrical, magnetic or electromagnetic field which can interact with an earthed object, such as an operator's or patient's finger approaching the button. For example, the touch sensor can be a capacitive or inductive sensor arrangement, as available from companies such as ANALOG DEVICE, CYPRESS, MAXIM and the like. Furthermore, it is possible to use sensors which work on the basis of changes in resistance or in a conduction value. In another embodiment, light-sensitive sensors for outputting the activation signal may be utilized.

Further embodiments can include using a control device which enables and/or disables functions of the device within a predetermined time after receiving the activation signal. For instance, if an activation signal is generated by the touch sensor and the button is not operated within a predetermined period of time, the button can be disabled because it is likely that the operator or patient activated the touch sensor unintentionally. On the other hand, if the button has not been operated for a predetermined period of time, it is likely that the activated display can, for example, be deactivated, since the patient may no longer be interested in the information displayed.

In one particular embodiment, a button can be provided with an incorporated touch sensor such that a first action of the device is activated by the non-contact-sensor or touch sensor generating the activation signal while a second action of the device is activated through the button.

For example, the first action may be the activation of a display, screen or backlight of the device and the second action may be administering a medicine dose, such as a medicine bolus. Alternatively, the first action may be the activation of the button and the second action may be the administration of a medicine bolus.

In such an embodiment, the device can also be configured to have a set of multiple buttons and a touch sensor that may be incorporated into one or multiple of those buttons. Accordingly, this embodiment of the device may comprise more than one touch sensor.

Furthermore, in another embodiment, the activation and/or deactivation of the touch sensor and/or button and/or display may be communicated to a user or operator of the device, i.e. the patient. For example, it is possible to output a sound signal, for instance, when the touch sensor is activated and outputs the activation signal.

It is also possible to output signals other than sound signals, such as visible signals, vibration signals, buzzer signals, or the like, which the user or operator will notice even when the device is placed in a pocket of the patient's clothing. Furthermore, it might be advantageous if the type of activation is communicated to the operator or patient. For instance, the type of signal outputted in the event of activation may be different for an activation signal which is within a predetermined range of values. If the touch sensor detects a detectable event which is not within a predetermined range, it is possible for a recognisable signal to be outputted in order to inform the operator or patient that something has happened which was close to activating the device to accept instructions inputted using the button. If the event detected by the touch sensor is suitable to allow a signal which is within the predetermined range, the activation signal is outputted and another type of recognisable signal can be brought to the patient's attention. Accordingly, the patient can learn what sort of events can affect the device in an arbitrary manner and should be avoided. Thus, for example, events such as putting keys into the pocket could be identified as actions which should be avoided because the keys could activate the button which is suitable for administering bolus doses.

It is also possible to program the controller such that a particular code has to be inputted via the touch sensor first, in order to activate the button or the display or other parts or functions of the device of the invention. For instance, one touch on the touch sensor could activate the display and two touches could activate the button itself (such as if the touches are applied to the sensor in sequence and within a certain time interval or time period). Any alternative type of "touch codes" could also be used.

Finally, it is also possible to use a "touch code" to activate the administration device or a function of the administration device and to then enter data or request data, also by touching or otherwise interacting with the touch sensor.

Figure 7A:
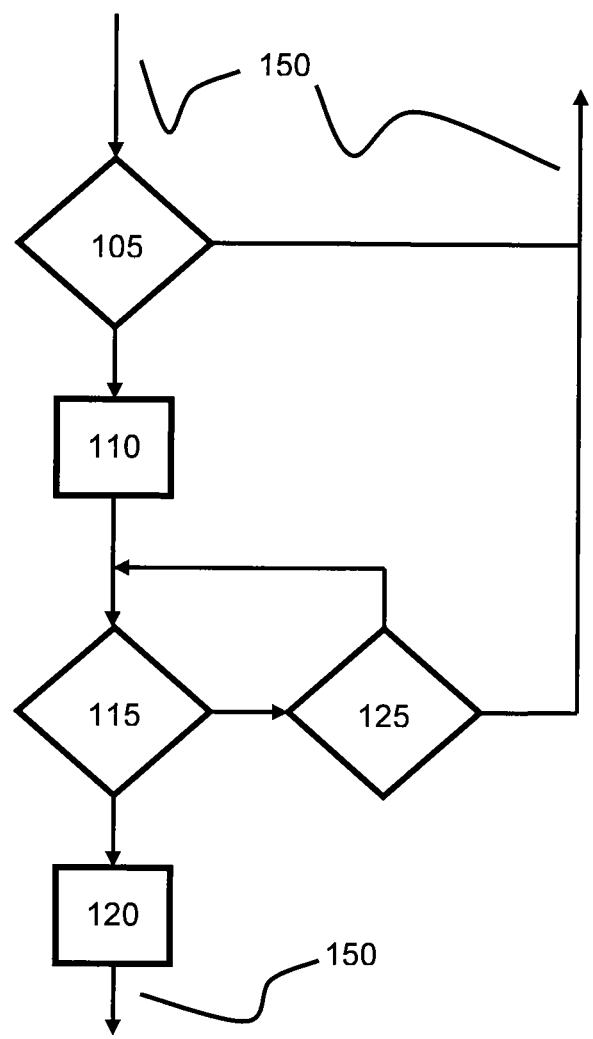
FIG. 7a depicts exemplary control flows according to one or more embodiments shown and described herein.
Figure 7B:
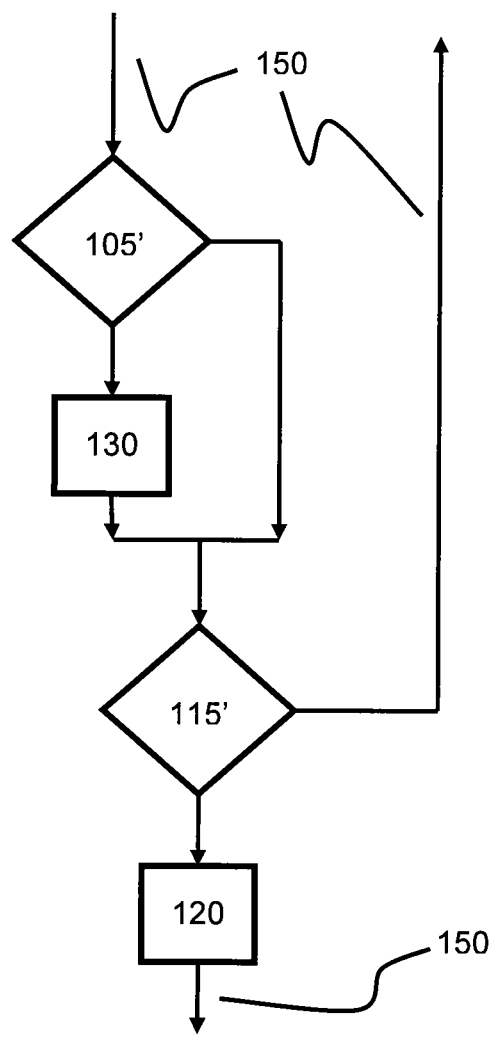
FIG. 7b depicts alternative exemplary control flows according to one or more embodiments shown and described herein.

Referring now to FIGS. 7a and 7b, a method is illustrated schematically demonstrating a control flow in accordance with the embodiments illustrated in FIGS. 3 and 4, respectively. As indicated by the arrows 150 to other parts of the control flow, the steps shown in FIG. 7a may be carried out repeatedly or substantially continuously in the framework of the overall control flow as controlled by the controller 14. In step 105, it can be checked if the touch sensor 20 is activated, (i.e., if it generates the activation signal). If this is not the case, the general control flow is continued. If the activation signal is generated in step 105, a timer such as a countdown timer is started to enable the button 18 for a predefined period of time. Next, in step 110, the display 16 may optionally be activated. In step 115, it may be checked if the button 18 is actuated (e.g., pressed) with the activation signal still being generated. If this is not the case, it is checked in step 125 if the timer indicates the predefined period of time for pressing the button 18 has elapsed. If this the case, the general control flow is continued. Otherwise, the step 115 is repeated. If the button 18 is detected to be pressed in step 115, the step of a medicine bolus administration may be carried out in step 120 before the general control flow is continued. If the display 16 has been activated in step 110, it may be switched off or otherwise deactivated at some point after the medicine bolus administration. In other embodiments, the steps 110 and 125 may be omitted all together. In this example, the touch sensor 20 may thereby be used as a safety feature for enabling the button 18.

Figure 5:
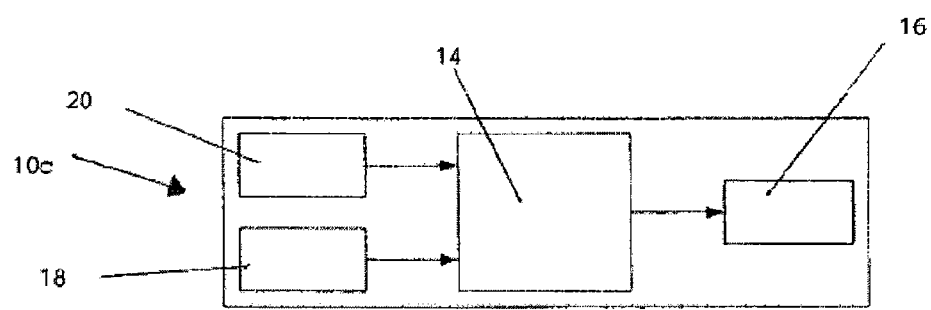
FIG. 5 schematically depicts parts of yet another administration device according to one or more embodiments shown and described herein.

In accordance with the embodiment of the device 10c illustrated in FIG. 5, the sensor 20 can generate an activation signal which is received by the controller 14. Upon receiving the activation signal from the touch sensor 20, the controller 14 can activate a display 16. As also illustrated in FIG. 3, the controller 14 can simultaneously or immediately thereafter also enable the button 18. However, in accordance with the embodiment in FIG. 5, this option can be omitted, and it is possible for the display 16 to be activated only by the activation signal 3 outputted by the touch sensor 20.

Referring now to FIG. 7b, a method is illustrated schematically showing a control flow for the embodiments illustrated in FIG. 5. In step 105', it can be checked if the touch sensor 20 is activated (i.e., the activation signal is generated). If this is the case, the display 16 may be activated in step 130. Independent of whether the display 16 has been activated or not, it can be checked in step 115' if the button 18 is actuated (e.g. pressed). If this is not the case, the general control flow can continue. If the button 18 is pressed, the step of a medicine bolus administration may be carried out in step 120 before the general control flow is continued. In such an embodiment, the touch sensor 20 may be used to activate the display only if required without having influence on the initiation of a medicine bolus administration via the button 18.

Figure 6:
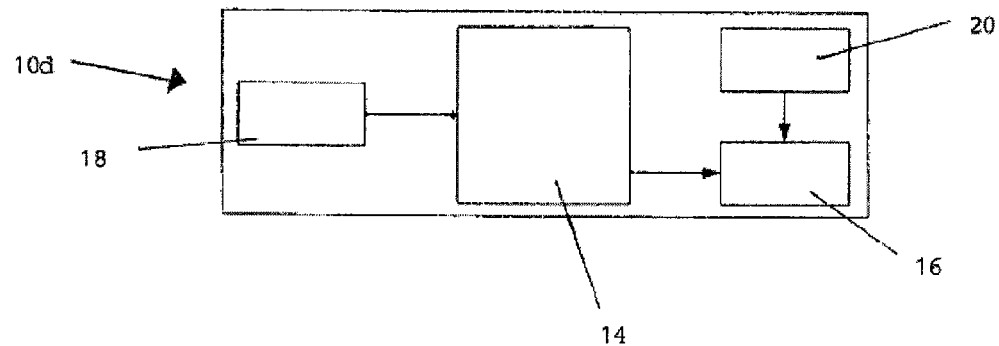
FIG. 6 schematically depicts parts of even yet another administration device according to one or more embodiments shown and described herein.

The embodiment illustrated in FIG. 6 relates to an infusion device 10d in which the touch sensor 20 directly activates the display 16. One or more buttons 18 can be used separately, without influencing the activation signal outputted by the sensor 20. However, it is also possible for the activation signal from the touch sensor 20 to also enable the button or buttons 18 for inputting information or data into the controller 14.

It is noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. An administration device for supplying an injectable or infusible product into an organism, the administration device comprising:
   a reservoir for storing the product;
   a supply device for supplying the product from the reservoir into the organism;
   a controller to control operation of the administration device;
   a button communicatively coupled to the controller to initiate at least one action of the administration device; and
   a touch sensor that generates an activation signal, wherein the touch sensor is incorporated into the button or is disposed in the vicinity of the button and is communicatively coupled to the button and/or the controller, and wherein the touch sensor is configured to activate the button with a touch code and to modify a basal administration schedule with a code; and
   wherein both the button and the touch sensor are mounted on a substantially flat printed circuit board which supports electrical circuits of the controller, and the touch sensor extends laterally out from the bottom of the button against the flat printed circuit board and is adhered to the flat printed circuit board.

2. The administration device of claim 1, further comprising configuring the administration device to be activated by a touch-code, and configuring the administration device for entering or requesting data by touching the touch sensor.

3. The administration device of claim 2, wherein a valid enabling of the button is communicated to a user or operator of the device.

4. The administration device of claim 1 further comprising a display that is activated by the activation signal.

5. The administration device of claim 1, wherein the touch sensor is a capacitive sensor or an inductive sensor.

6. The administration device of claim 1, wherein the touch sensor is a sensor that detects a change in resistance, a change in conduction value, a change in light intensity, or combinations thereof.

7. The administration device of claim 1 further comprising a housing disposed proximate the touch sensor.

8. The administration device of claim 7, wherein the housing comprises a material that does not absorb or shield electrical, electromagnetic or magnetic fields.

9. The administration device of claim 1, wherein the controller enables and/or disables functions of the administration device within a predetermined period of time after receiving the activation signal.

10. The administration device of claim 1, wherein the touch sensor is activated and/or deactivated based on its sensitivity.

11. The administration device of claim 10, wherein the touch sensor is variable with respect to its sensitivity.

12. The administration device of claim 1, further comprising a display configured to be activated by the controller when a code is inputted via the touch sensor.

13. The administration device of claim 1, wherein the controller initiates a first action of the administration device upon the touch sensor generating the activation signal and the controller initiates a second action of the administration device upon the button being actuated.

14. The administration device of claim 1, wherein the controller initiates the administration of a medicine bolus if the button is actuated with the activation signal being generated and the controller does not initiate the administration of the medicine bolus if the button is actuated without the activation signal being generated.

15. A method for controlling operation of an administration device, the comprising:
   detecting if a touch sensor is activated, the touch sensor being incorporated into a button or being disposed proximate the button, wherein activating the touch sensor generates an activation signal, wherein both the button and the sensor are mounted on a substantially flat printed circuit board which supports electrical circuits of the controller, and the touch sensor extends laterally out from the bottom of the button against the flat printed circuit board and is adhered to the flat printed circuit board;
   detecting if the button is being actuated; and
   initiating an action of the administration device in dependence of the touch sensor being activated or not activated and the button being pressed or not pressed; and wherein the touch sensor is configured to activate the button with a touch code and to modify a basal administration schedule with a code.

16. The method of claim 15, further comprising administering a medicine bolus if the button is actuated with the activation signal being generated and not administering the medicine bolus if the button is actuated without the activation signal being generated.

17. The method of claim 15, further comprising activating a display upon the activation signal being generated and administering a drug bolus upon the button being actuated.

18. An administration device for supplying an injectable or infusible product into an organism, the administration device comprising:
- a reservoir for storing the product;
- a supply device for supplying the product from the reservoir into the organism;
- a controller to control operation of the administration device;
- a button communicatively coupled to the controller to initiate at least one action of the administration device; and
- a touch sensor that generates an activation signal, wherein the touch sensor is incorporated into the button or is disposed in the vicinity of the button and is communicatively coupled to the button and/or the controller, wherein the touch sensor is a capacitive sensor or an inductive sensor, and wherein the touch sensor is configured to activate the button with a touch code and to modify a basal administration schedule with a code; and
- wherein both the button and the sensor are mounted on a substantially flat printed circuit board which supports electrical circuits of the controller, the touch sensor extending laterally out from the bottom of the button against the flat printed circuit board, and wherein the touch sensor is adhered to the flat printed circuit board.

19. The administration device of claim 18, wherein a valid enabling of the button is communicated to a user or operator of the device.

20. The administration device of claim 18 further comprising a display that is activated by the activation signal.

* * * * *

UNITED STATES PATENT AND TRADEMARK OFFICE
CERTIFICATE OF CORRECTION

PATENT NO. : 8,974,435 B2  
APPLICATION NO. : 12/912817  
DATED : March 10, 2015  
INVENTOR(S) : Kurt Friedli Page 1 of 2

It is certified that error appears in the above-identified patent and that said Letters Patent is hereby corrected as shown below:

In the specification

Col. 2, Line 26,
"large number of unintended operations of a the unstable but-" should read
--large number of unintended operations of the instable but- --;

Col. 2, Line 29,
"tion may be prevented by providing at least too buttons which" should read
--tion may be prevented by providing at least two buttons which--;

Col. 3, Line 11,
"structure is indicated with life reference numerals and in" should read
--structure is indicated with like reference numerals and in--;

Col. 4, Line 1,
"actuated (e.g., pressed) with a certain fore and/or travel a" should read
--actuated (e.g., pressed) with a certain force and/or travel a--;

Col. 4, Line 56,
"22 of the infusion device 10 can accommodates all the differ-" should read
--22 of the infusion device 10 can accommodate all the differ- --;

Col. 4, Line 66,
"enablement or disablement the push button 18 via the button." should read
--enablement or disablement of the push button 18 via the button.--;

Col. 5, Line 3,
"embodiment allows for the enablement or disablement the" should read
--embodiment allows for the enablement or disablement of the--;

Signed and Sealed this  
Twenty-third Day of February, 2016

Michelle K. Lee  
*Director of the United States Patent and Trademark Office*

CERTIFICATE OF CORRECTION (continued)
U.S. Pat. No. 8,974,435 B2

In the specification

Col. 5, Line 5,
  "the enabling or disabling the button 18, the touch sensor 20" should read
  --by enabling or disabling the button 18, the touch sensor 20--;

Col. 5, Line 43,
  "LED 26 (as illustrated in FIG. 1, in order to inform the patient" should read
  --LED 26 (as illustrated in FIG. 1), in order to inform the patient--;

Col. 6, Line 12,
  "object, such as a cloths fabric or a key which is stored in the" should read
  --object, such as a clothes fabric or a key which is stored in the--;

Col. 6, Line 19,
  "the administration of a medicine bolus, and to active the" should read
  --the administration of a medicine bolus, and to activate the--; and In the claims Col. 10, Claim 15, Line 42,
  "device, the comprising:" should read
  --device comprising:--.